United States Patent [19]
Amiot

[11] Patent Number: 5,955,353
[45] Date of Patent: Sep. 21, 1999

[54] HOLLOW FIBER BIOREACTOR WITH AN EXTRAFILAMENT FLOW PLUG

[75] Inventor: Bruce P. Amiot, Coon Rapids, Minn.

[73] Assignee: Excorp Medical, Inc., Oakdale, Minn.

[21] Appl. No.: 08/861,503

[22] Filed: May 22, 1997

[51] Int. Cl.⁶ .................................................. C12M 3/06
[52] U.S. Cl. ...................... 435/297.4; 435/370; 435/400; 604/4; 210/321.81
[58] Field of Search ..................................... 435/366, 370, 435/400, 401, 297.2, 297.4, 299.1; 210/321.8, 321.81, 321.89, 321.9; 604/4, 5

[56] References Cited

U.S. PATENT DOCUMENTS

| | | |
|---|---|---|
| 3,734,851 | 5/1973 | Matsumura . |
| 3,883,393 | 5/1975 | Knazek et al. . |
| 4,220,725 | 9/1980 | Knazek et al. . |
| 4,241,187 | 12/1980 | White . |
| 4,293,413 | 10/1981 | Schnell . |
| 4,488,911 | 12/1984 | Luck et al. . |
| 4,514,499 | 4/1985 | Noll . |
| 4,537,860 | 8/1985 | Tolbert et al. . |
| 4,559,304 | 12/1985 | Kasai et al. . |
| 4,647,539 | 3/1987 | Bach . |
| 4,675,002 | 6/1987 | Viles et al. . |
| 4,692,411 | 9/1987 | Ghose . |
| 4,720,462 | 1/1988 | Rosenson . |
| 4,804,628 | 2/1989 | Cracauer et al. . |
| 4,833,083 | 5/1989 | Saxena . |
| 4,837,379 | 6/1989 | Weinberg . |
| 4,861,485 | 8/1989 | Fecondini . |
| 4,873,033 | 10/1989 | Heckmann et al. . |
| 4,923,598 | 5/1990 | Schül . |
| 4,959,148 | 9/1990 | Clark, III . |
| 4,999,298 | 3/1991 | Wolfe et al. . |
| 5,013,437 | 5/1991 | Trimmer et al. . |
| 5,015,585 | 5/1991 | Robinson . |
| 5,043,260 | 8/1991 | Jauregui . |
| 5,064,764 | 11/1991 | Besnainon et al. . |
| 5,106,743 | 4/1992 | Franzblau et al. . |
| 5,108,923 | 4/1992 | Benedict et al. . |
| 5,108,926 | 4/1992 | Klebe . |

(List continued on next page.)

FOREIGN PATENT DOCUMENTS

| | | |
|---|---|---|
| 0 155 237 A2 | 9/1985 | European Pat. Off. . |
| 0 380 610 B1 | 8/1990 | European Pat. Off. . |
| 42 06 585 A1 | 9/1993 | Germany . |
| 4-341176 | 11/1992 | Japan ................................. 435/297.4 |
| 2 178 447 | 2/1987 | United Kingdom . |
| WO 89/00188 | 1/1989 | WIPO . |
| WO 89/11529 | 11/1989 | WIPO . |
| WO 92/07615 | 5/1992 | WIPO . |
| WO 96/30492 | 10/1996 | WIPO . |
| WO 96/39817 | 12/1996 | WIPO . |
| WO 97/16527 | 5/1997 | WIPO . |

OTHER PUBLICATIONS

Akimoto et al., "Fundamental Studies on Biological Artificial Liver Support; Liver Functions of Entrapped Hepatocytes," *Jpn. J. Artif. Organs*, 14(1):249–252 (1985).

Anderson et al., "Cell–Mediated Contraction of Collagen Lattices in Serum–Free Medium: Effect of Serum and Non–serum Factors," *In Vitro Cell Dev. Biol.*, 26:61–66 (Jan. 1990).

(List continued on next page.)

*Primary Examiner*—William H. Beisner
*Attorney, Agent, or Firm*—Popovich & Wiles, P.A.

[57] ABSTRACT

A bioreactor containing living animal cells at a density approaching that of normal animal tissue is described. High cell loading is achieved by providing a flow restrictor which controls fluid flow through the bioreactor during cell loading. Methods for making and using the bioreactor are also described.

42 Claims, 9 Drawing Sheets

U.S. PATENT DOCUMENTS

| | | |
|---|---|---|
| 5,116,493 | 5/1992 | Chick et al. . |
| 5,198,110 | 3/1993 | Hanai et al. . |
| 5,211,849 | 5/1993 | Kitaevich et al. . |
| 5,213,720 | 5/1993 | Civerchia . |
| 5,240,614 | 8/1993 | Ofsthun et al. . |
| 5,254,249 | 10/1993 | Terada et al. . |
| 5,254,471 | 10/1993 | Mori et al. . |
| 5,270,192 | 12/1993 | Li et al. . |
| 5,290,684 | 3/1994 | Kelly . |
| 5,368,555 | 11/1994 | Sussman et al. . |
| 5,376,548 | 12/1994 | Matsuo et al. ......................... 435/299.1 |
| 5,411,662 | 5/1995 | Nicolas, Jr. et al. . |
| 5,480,552 | 1/1996 | Soltys et al. . |
| 5,510,254 | 4/1996 | Naughton et al. . |
| 5,510,257 | 4/1996 | Sirkar et al. . |
| 5,512,474 | 4/1996 | Clapper et al. . |
| 5,516,691 | 5/1996 | Gerlach . |
| 5,527,467 | 6/1996 | Ofsthun et al. . |
| 5,536,656 | 7/1996 | Kemp et al. . |
| 5,595,909 | 1/1997 | Hu et al. . |
| 5,605,835 | 2/1997 | Hu et al. ............................. 435/299.1 |
| 5,643,794 | 7/1997 | Liu et al. . |
| 5,658,797 | 8/1997 | Bader . |
| 5,700,372 | 12/1997 | Takesawa et al. ................. 210/321.81 |
| 5,730,712 | 3/1998 | Falkvall et al. ............................ 604/5 |

OTHER PUBLICATIONS

Bell et al., "Production of a Tissue–like Structure by Contraction of Collagen Lattices by Human Fibroblasts of Different Proliferative Potential In Vitro," *Proc. Natl. Acad. Sci. USA*, 76(3):1274–1278 (Mar. 1979).

Block et al., "D–Galactosamine–Induced Liver Injury in Large Dogs: is it really Fulminant Liver Failure?," Submitted Abstract to Oct. 1996 AASLD Meeting.

Block et al., "Preclinical Evaluation of a Novel Extracorporeal Bioartificial Liver Device (BAL)," Submitted Abstract to Oct. 1996 AASLD Meeting.

Catapano, "Mass Transfer Limitations to the Performance of Membrane Bioartificial Liver Support Devices," *The International Journal of Artificial Organs*, 19(1):18–35 (1996).

Chari et al., "Brief Report: Treatment of Hepatic Failure with Ex Vivo Pig–Liver Perfusion Followed by Liver Transplantation," *The New England Journal of Medicine*, 331(4):234–269 (Jul. 28, 1994).

Demetriou et al., "Early Clinical Experience with a Hybrid Bioartificial Liver," Artificial Liver Support, Scand. J. Gastroenterol. Suppl., 208(1):111–117 (1995).

Demetriou et al., "New Method of Hepatocyte Transplantation and Extracorporeal Liver Support," *Ann. Surg.*, 204(3):259–271 (Sep. 1986).

Dixit, "Development of a Bioartificial Liver Using Isolated Hepatocytes," *Artificial Organs*, 18(5):371–384 (1994).

Dixit, "Transplantation of Isolated Hepatocytes and Their Role in Extrahepatic Life Support Systems," *Scand J. Gastroenterol*, 30 Suppl. 208:101–110 (1995).

Eiseman et al., "Hepatocyte Perfusion Within Centrifuge," *Surgery, Gynecology & Obstetrics*, 142:21–28 (Jan. 1976).

Fernandez–Bueno, "Development of an Extracorporeal Liver Support System: Initial Results," *Military Medicine*, 157(4):180–182 (Apr. 1992).

Fuchs, "Amino Acid Metabolism by Hepatocytes in a Hybrid Liver Support Bioreactor," *The International Journal of Artificial Organs*, 17(12):663–669 (1994).

Gerlach et al., "Bioreactor for a Larger Scale Hepatocyte in Vitro Perfusion," *Transplantation*, 58(9):984–988 (Nov. 15, 1994).

Gerlach et al., "Gas Supply Across Membranes in Bioreactors for Hepatocyte Culture," *Artificial Organs*, 14(5):328–333 (1990).

Gerlach et al., "Hybrid Liver Support System in a Short Term Application on Hepatectomized Pigs," *The International Journal of Artificial Organs*, 17(10):549–553 (1994).

Guidry et al., "Studies on the Mechanism of Hydrafted Collagen Gel Reorganization by Human Skin Fibroblasts," *J. Cell. Sci.*, 79:67–81 (1985).

Hu et al., "Cultivation of Hepatocytes in a New Entrapment Reactor: a Potential Bioartificial Liver," *Animal Cell Culture and Production of Biologicals*, 75–80 (1991).

Hu et al., "Enhancement of Cytochrome P450 Function of Collagen Entrapped Hepatocytes by the Addition of Liver Extracellular Matrix Components," Cell Transplant Society, Second International Congress, Minneapolis, May 1994.

Jauregui, "Treatment of Hepatic Insufficiency Based on Cellular Therapies," *The International Journal of Artificial Organs*, 14(6):321–326 (1991).

Jauregui et al., "Use of Mammalian Liver Cells for Artificial Liver Support," *Cell Transplantation*, 5(3):353–367 (1996).

Koshino et al., "A Biological Extracorporeal Metabolic Device for Hepatic Support," *Trans. Amer. Soc. Artif. Int. Organs*, 20:492–500 (1975).

LePage et al., "A Bioartificial Liver Used as a Bridge to Liver Transplantation in a 10–Year–Old Boy," *American Journal of Critical Care*, 3(3):224–227 (May 1994).

LePage et al., "Plasma Separation for Artificial Liver Support," *Journal of Clinical Apheresis*, 10:70–75 (1995).

Li et al., "Culturing of Primary Hepatocytes as Entrapped Aggregates in a Packed Bed Bioreactor: A Potential Bioartificial Liver," *In Vitro Cell. Dev. Biol.*, 29A:249–254 (Mar. 1993).

Lie et al., "Successful Treatment of Hepatic Coma by a New Artificial Liver Device in the Pig," *Res. Exp. Med.*, 185:483–494 (1985).

Matthew et al., "Microencapsulated Hepatocytes," *Trans. Am. Soc. Artif. Intern. Organs*, 37:M328–M330 (1991).

Matthew et al., "Performance of Plasma–Perfused, Microencapsulated Hepatocytes: Prospects for Extracorporeal Liver Support," *Journal of Pediatric Surgery*, 28(11):1423–1428 (Nov. 1993).

McGuire et al., "Review of Support Systems Used in the Management of Fulminant Hepatic Failure," *Dig. Dis.*, 13:379–388 (1995).

Mito, "Hepatic Assist: Present and Future," *Artificial Organs*, 10(3):214–218 (1986).

Miura et al., "Characterization of Immobilized Hepatocytes as Liver Support," *Biomat., Art. Cells, Art. Org.*, 18(4):549–554 (1990).

Miura et al., "Synthesis and Secretion of Protein by Hepatocytes Entrapped within Calcium Alginate," *Artificial Organs*, 10(6):460–465 (Dec. 1986).

Miyoshi et al., "Long–Term Continuous Culture of Hepatocytes in a Packed–Bed Reactor Utilizing Porous Resin," *Biotechnology and Bioengineering*, 43:635–644 (1994).

Morsiani et al., "Automated Liver Cell Processing Facilitates Large Scale Isolation and Purification of Porcine Hepatocytes," *ASAIO Journal*, 41(2):155–161 (Apr.–Jun. 1995).

Neuzil et al., "Use of a Novel Bioartificial Liver in a Patient with Acute Liver Insufficiency," *Surgery*, 113(3):340–343 (Mar. 1993).

Nyberg et al., "Bilirubin Conjugation in a Three Compartment Hollow Fiber Bioreactor," *Annual International Conference of the IEEE Engineering in Medicine and Biology Society*, 12(1):0443–0444 (1990).

Nyberg et al., "Demonstration of Biochemical Function by Extracorporeal Xenohepatocytes in an Anhepatic Animal Model," *Transplantation Proceedings*, 25(2):1944–1945 (Apr. 1993).

Nyberg et al., "Evaluation of a Hepatocyte–Entrapment Hollow Fiber Bioreactor: A Potential Bioartificial Liver," *Biotechnology and Bioengineering*, 41:194–203 (1993).

Nyberg et al., "Extracorporeal Application of a Gel–Entrapment, Bioartificial Liver: Demonstration of Drug Metabolism and Other Biochemical Functions," *Cell Transplantation*, 2:441–452 (1993).

Nyberg et al., "Hepatocyte Culture Systems for Artificial Liver Support: Implications for Critical Care Medicine (Bioartificial Liver Support)," *Critical Care Medicine*, 20(8):1157–1168 (Aug. 1992).

Nyberg et al., "Immunoprotection of Xenocytes in a Hollow Fiber Bioartificial Liver," *ASAIO Journal*, pp. M463–M467 (1992).

Nyberg et al., "Matrigel Improves Function of Gel–Entrapped Hepatocytes: Implications for the Hollow Fiber Bioartificial Liver," *Hepatology*, 16:286A (1992).

Nyberg et al., "Microelectrode Measurement of Oxygen Tensions in Collagen–Hepatocyte Gels," *Biotechnology Techniques*, 5(6):449–452 (1991).

Nyberg et al., "Pharmacokinetic Analysis Verifies P450 Function During In Vitro and In Vivo Application of a Bioartificial Liver," *ASAIO Journal*, pp. M252–M256 (1993).

Nyberg et al., "Rapid Determination of Hepatocyte Viability with FDA Staining and Flow Cytometry," *The American Journal of Gastroenterology*, 86:1134 (1991).

Nyberg et al., "Staining with Fluorescein Diacetate Correlates with Hepatocyte Function," *Biotechnic & Histochemistry*, 68(1):56–63 (1993).

Olumide et al., "Hepatic Support with Hepatocyte Suspensions in a Permeable Membrane Dialyzer," *Surgery*, 82(5):599–606 (Nov. 1977).

Rozga et al., "Development of a Bioartificial Liver: Properties and Function of a Hollow–Fiber Module Inoculated with Liver Cells," *Hepatology*, 17(2):258–265 (1993).

Rozga et al., "Development of a Hybrid Bioartificial Liver," *Annals of Surgery*, 217(5):502–511 (May 1993).

Rozga et al., "Isolated Hepatocytes in a Bioartificial Liver: A Single Group View and Experience," *Biotechnology and Bioengineering*, 43:645–653 (1994).

Scholz et al., "A Two–Compartment Cell Entrapment Bioreactor with Three Different Holding Times for Cells, High and Low Molecular Weight Compounds," *Cytotechnology*, 4:127–137 (1990).

Shatford et al., "A Hepatocyte Bioreactor as a Potential Bioartificial Liver: Demonstration of Prolonged Tissue–Specific Functions," *Surgical Forum*, vol. XLII, pp. 55–56 (Proceedings of the 47th Annual Sessions of the Forum on Fundamental Surgical Problems 1991 Clinical Congress, Oct. 20–25, Chicago).

Shatford et al., "Hepatocyte Function in a Hollow Fiber Bioreactor: A Potential Bioartificial Liver[1,2]," *Journal of Surgical Research*, 53:549–557 (1992).

Shiraha et al., "Improvement of Serum Amino Acid Profile in Hepatic Failure with the Bioartificial Liver Using Multicellular Hepatocyte Spheroids," *Biotechnology and Bioengineering*, 50:416–421 (1996).

Shnyra et al., "Bioartificial Liver Using Hepatocytes on Biosilon Microcarriers: Treatment of Chemically Induced Acute Hepatic Failure in Rats," *Artificial Organs*, 15(3):189–197 (1991).

Shnyra et al., "Large–Scale Production and Cultivation of Hepatocytes on Biosilon Microcarriers," *Artificial Organs*, 14(6):421–428 (1990).

Sielaff et al., "An Anesthetized Model of Lethal Canine Galactosamine Fulminant Hepatic Failure," *Hepatology*, 00(0):1–9 (1995).

Sielaff et al., "Application of a Bioartificial Liver (BAL) in a New Model of Acute Fulminant Hepatitis," *American College of Surgeons, Annual Meeting*, (Oct. 1993).

Sielaff et al., "Gel–Entrapment Bioartificial Liver Therapy in Galactosamine Hepatitis," *Journal of Surgical Research* 59:179–184 (1995).

Sussman et al., "Extracorporeal Liver Support," *J. Clin. Gastroenterol*, 18(4):320–324 (1994).

Takabatake et al., "Encapsulated Multicellular Spheroids of Rat Hepatocytes Produce Albumin and Urea in a Spouted Bed Circulating Culture System," *Artificial Organs*, 15(6):474–480 (1991).

Takahashi et al., "Does a Porcine Hepatocyte Hybrid Artificial Liver Prolong the Survival Time of Anhepatic Rabbits," *ASAIO Journal*, pp. M468–M472 (1992).

Takeshita et al., "High Cell–Density Culture System of Hepatocytes Entrapped in a Three–Dimensional Hollow Fiber Module with Collagen Gel," *Artificial Organs*, 19(2):191–193 (1995).

Williams et al., "Intensive Liver Care and Management of Acute Hepatic Failure," *Digestive Diseases and Sciences*, 36(6):820–826 (Jun. 1991).

Wolf et al., "Bilirubin Conjugation by an Artificial Liver Composed of Cultured Cells and Synthetic Capillaries," *Trans. Amer. Soc. Artif. Int. Organs*, 21:16–26 (1975).

Yanagi et al., "A High Density Culture of Hepatocytes Using a Reticulated Polyvinyl Formol Resin," ASAIO Transactions, 36:M727–M729 (1990).

Yanagi et al., "Performance of a New Hybrid Artificial Liver Support System Using Hepatocytes Entrapped Within a Hydrogel," *Trans. Am. Soc. Artif. Intern. Organs*, 35:570–572 (1989).

Jauregui et al., "Adult Rat Hepatocyte Cultures as the Cellular Component of an Artificial Hybrid Liver," *Biomaterials in Artificial Organs*, (J.P. Paul et al., eds. Macmillan) Chapter 18, pp. 130–140 (1984).

Jauregui et al., "Hybrid Artificial Liver", *Biocompatible Polymers, Metals and Other Composites*, (Ed. M. Szycher, Tecnomic Pub., Lancaster, PA) Chapter 39, pp. 907–928 (1983).

Sielaff et al., "Canine Galactosamine Hepatitis", *Hepatology,* Abstract, 21(3):796–804 (Mar. 1995).

Sielaff et al., "Characterization of the Three Compartment Gel Entrapment Porcine Hepatocyte Bioartificial Liver," *Cell Biol. Toxicol.,* 13(4–5):357–364 (Jul. 1997).

Sielaff et al., "Gel–entrapment Bioartificial Liver Therapy in Galactosamine Hepatitis[1]," *J. Surg. Res.,* 59(1):179–184 (Jul. 1995).

Sielaff et al., "A Technique for Porcine Hepatocyte Harvest and Description of Differentiated Metabolic Functions in Static Culture[1]", *Transplantation,* 59(10):1459–1463 (May 27, 1995).

HOLLOW FIBER BIOREACTOR WITH AN EXTRAFILAMENT FLOW PLUG

FIELD OF THE INVENTION

The present invention is in the field of bioreactors. More particularly, the present invention relates to bioreactors loaded with animal cells at a density which approaches that of normal animal tissue.

BACKGROUND

Hollow fiber bioreactor cartridges typically include a housing, often cylindrical in shape, that contain a plurality of hollow fibers or filaments. The filaments are formed of a material which allows molecular transport through the filament wall. Such materials typically include polysulfones, cellulose acetates and the like. The cartridges usually define two spaces: an intrafilament space (defined by the lumens of the filaments) and an extrafilament space (defined by exterior of the filaments and the interior of the cartridge housing). The intrafilament space defines a filament flow path which communicates with at least a filament inlet port and a filament outlet port, and the extrafilament space defines an extrafilament flow path which communicates with at least a housing inlet port and a housing outlet port. Communication between the flow paths is limited to molecular transport through the walls of the filaments.

The use of bioreactors containing live cells is known in the art. Typically, the cells are loaded into the extrafilament space and often contained or encapsulated within a supporting matrix. Numerous types of cells have been used, including hepatocytes.

In one mode of use, a biological fluid to be treated, such as blood, is circulated through the filament flow path. If the bioreactor is to act as an artificial liver, the cells are hepatocytes, often harvested from pigs. As the blood flows through the filaments, molecular transport occurs across the filament walls, thereby removing contaminants from the blood. Such systems are often configured with the blood traveling in a fluid circuit from a patient, to the bioreactor and back to the patient. If desired, although not typical, a nutrient solution for the cells can circulated through the extrafilament flow path simultaneously with blood flow through the filaments. The flows may be countercurrent, co-current or crosscurrent flows.

One problem that exists with bioreactors of the type described above is that it is very difficult to construct them with adequate cell uniformity and cell loading density. Thus, bioreactors of the types commonly in use include cells which are seeded into the reactor at low densities and then allowed to grow to confluence. Alternatively, cells are sometimes encapsulated or attached to biocarriers and injected into the bioreactor interior. In each of these embodiments, it has been found to be very difficult to obtain a cell density greater than about $10^5$ cells/ml. Since the resulting bioreactors have cell densities several orders of magnitude less than those of normal animal tissue, less than ideal results have been obtained.

As noted above, it has been found to be very difficult to load bioreactors to high cell densities. The basis for this difficulty is as follows. Bioreactor cartridges may include thousands of hollow filaments which are assembled into a cylindrical bundle and then inserted into the cartridge housing. In order to maximize the area of the transport membrane, the filaments are loaded into the housing at very high packing densities. The resulting extrafilament space comprises thousands of very small, narrow passageways between the densely packed filaments. The resulting geometry makes it very difficult to pump viscous fluids through the extrafilament flow path. While lower viscosity fluids can be used, such fluids often do not offer a sufficiently high cell density to produce a device that is viable in clinical settings. However, fluids capable of providing cell densities approaching those of normal animal tissue (i.e., $10^8$ cells per milliliter) suffer from an inability to sufficiently infiltrate the extrafilament space. In particular, the use of such high density fluids is often subject to flow shunting in which the fluid will stream directly along the interior wall of the housing, resulting in cell loading of only about 10 to 20% of the available extrafilament space.

Thus, a need exists for a bioreactor that is capable of maintaining living animal cells at a density approaching that of normal animal tissue. A need also exists for a bioreactor that is adapted to be filled with a high cell density in a manner that is simple and results in uniform cell distribution.

SUMMARY OF THE INVENTION

The present invention relates to a bioreactor which includes a flow restrictor to aid in the uniform, high density loading of living animal cells. More particularly, the present invention relates to a bioreactor having an elongate housing defining a central axis. A plurality of elongate hollow filaments are positioned within the housing substantially parallel to the central axis. The filaments define an extrafilamentary space within the housing and are formed of a material which allows molecular transport across the filament wall. Cells, such as hepatocytes, inhabit the extrafilamentary space at a density approaching that of normal tissue. The bioreactor is also provided with a filament inlet port and a filament outlet port, each communicating through the hollow filaments to define a filament flow path, as well as a housing inlet port and a housing outlet port, each communicating through the extrafilamentary space to define an extrafilament flow path. The extrafilament flow path is isolated from the filament flow path such that a material in one path may enter the other path only by molecular transport through the hollow filament walls. Additionally, the device is provided with a flow restrictor positioned in the extrafilament flow path to maintain a substantially uniform flow across the extrafilament flow path.

The flow restrictor has been found to be useful in reducing or eliminating the flow shunting problems associated with the bioreactors of the prior art. In particular, it has been found that if a large, uniform flow resistance is provided in the extrafilament flow path, preferably at least adjacent to the housing outlet port, near plug-flow conditions can be achieved in the extrafilament flow path. Such flow conditions are conducive to uniform, high density cell loading in the extrafilament space.

The flow restrictor is preferably a hydrogel plug positioned in the extrafilament space in such a manner as to restrict fluid flow through the housing outlet port and in the extrafilament space adjacent to the housing outlet port. The plug is preferably formed in situ by introducing a gellable material into the extrafilament space, causing the material to migrate to a position adjacent to the housing outlet port, and gelling the material. Since the plug is positioned only in the extrafilament space, it does not restrict flow through the hollow filaments, and thus allows a high volume of a fluid to be treated to be passed through the device during clinical use.

DETAILED DESCRIPTION

Figure 1:
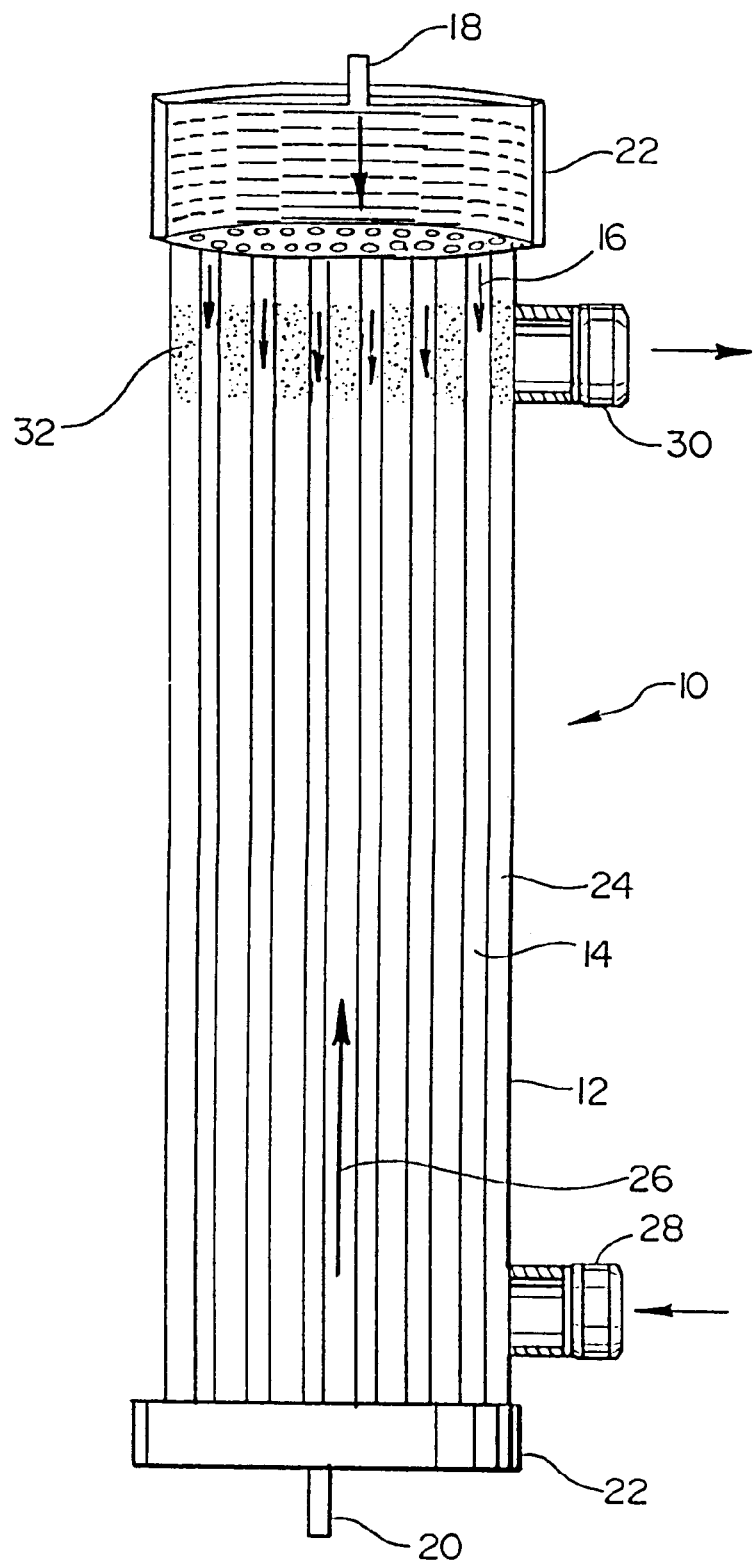
FIG. 1 is a schematic representation of a bioreactor of the present invention.

A bioreactor of the present invention in depicted schematically in FIG. 1. In FIG. 1, the bioreactor 10 includes a housing 12 containing a plurality of hollow filaments 14. The housing 12 defines a central axis, and the filaments 14 are positioned in the housing in a manner such that they run generally parallel to the central axis. The housing may be formed of any of a wide variety of biocompatible materials, including but not limited to acrylics, polycarbonates, polysulfones, styrene-acrylonitriles, and the like. Housing materials which are transparent to allow visualization of the interior of the device are preferred. Furthermore, if photoactive processes, discussed below, are to be used in the fabrication of the device, the use of a transparent housing greatly simplifies the fabrication process.

The filaments 14 are hollow tubes having a central lumen. Typically, the filaments have an external diameter on the order of about 210 to 250 microns, however, filaments having external diameters as large as about 1 to 2 mm can be used as well. The filaments typically have a lumen diameter on the order of about 190 to 220 microns, however diameters of up to about 800 to 1800 microns can also be used. The housing typically has a length in the range of approximately 20 to 30 cm to accommodate filaments having a length in the range of approximately 16 to 26 cm. The housing typically has an internal diameter of approximately 5 to 10 cm, allowing it to accommodate approximately 10,000 to 20,000 filaments. Of course, it is noted that the above dimensions are provided for reference only, and are not intended to limit the scope of the invention.

The filaments are formed of a biocompatible material through which molecular transfer can occur. For example, the filaments may be formed from polysulfones, cellulose acetates and the like. Other filament materials include polyacrylonitriles, polymethylmethacrylates (PMMA), ethylene polyvinyl alcohol copolymers (EVAL) as well as other materials routinely used to make hemodialysis and similar membranes. The lumens of the filaments define a filament flow path, depicted by arrows 16, which is in communication with a filament inlet port 18 and a filament outlet port 20. The filament inlet and outlet ports are preferably positioned in end caps 22 sealingly positioned at opposite ends of the housing 12.

The space between the exterior of the filaments 14 and the interior of the housing 12 is referred to herein as the extrafilament space 24. The extrafilament space 24 defines an extrafilament flow path, depicted by arrow 26 which is in communication with a housing inlet port 28 and a housing outlet port 30. The housing inlet and outlet ports are preferably located adjacent to the opposite ends of the housing 12. It is noted that the arrangement of the filament inlet and outlet ports and the housing inlet and outlet ports depicted in FIG. 1 is such that countercurrent flow between the filament flow path and the extrafilament flow path is established. It should be noted that the filament inlet port 18 may serve as an outlet and the filament outlet port 20 may serve as an inlet, thereby reversing the direction of the filament flow path 16 and establishing cocurrent flow between the filament flow path and the extrafilament flow path. As will be discussed in detail below, the extrafilament space 24 contains living cells present at a density approximating that of normal animal tissue. It is noted that for some cells, such as hepatocytes, extracellular matrices, such as collagen, fibronectin, laminin and the like be used to better support the cells. In such situations, the extracellular matrix can be mixed with the cells and infused into the reactor simultaneously with infusion of the cells themselves.

A flow restrictor 32 is positioned at least adjacent to the housing outlet port 30. The restrictor typically comprises a biocompatible hydrogel. As will be discussed in detail below, the restrictor can be formed in situ using various methods. The restrictor serves as a partial barrier in the extrafilament flow path, and as such, establishes plug-flow conditions in the extrafilament space. Such conditions have been found to greatly assist in providing uniform, high density cell loading in the extrafilament space. As used herein, the term "at least adjacent to the housing outlet port" is intended to mean that the flow restrictor is positioned in a manner such that it restricts the flow of fluid through the housing outlet. Such positioning may be simply in the region of the housing at which the port is located, or it may encompass a larger area, extending a short distance into the extrafilament space toward the housing inlet port 28.

As noted above, the flow restrictor 32 may be formed of any of a wide variety of biocompatible hydrogels. These include, but are not limited to collagen, agarose, calcium alginate, chitosan acetate, polyacrylamides, and combinations thereof. It is preferred that the hydrogel comprise at least about 90% water and less than about 10% polymer. In general, the flow restrictor preferably comprises a biocompatible hydrogel which will gel under gentle conditions, at temperatures below about 50° C., without the use of organic solvents. Gels formed by various methods including photoactivation, aqueous catalysis, and the like can be used.

In the case of collagen, the gel is preferably formed of Type-I bovine collagen such as Vitrogen-100 available from Collagen Corporation of Palo Alto, Calif. The material comes as a stock 3.0 mg/ml solution and has been shown to maintain gellability even when diluted 1:10 with a tissue culture medium.

Agarose is a purified form of agar, and is available from a wide variety of sources, such as Sigma Chemical Company of St. Louis, Mo. Agarose is typically obtained in a powdered form which can be dissolved in a warm solution of water or tissue culture medium. Agarose will gel at room temperature in concentrations of about 0.1 to 3.0% w/v.

Calcium alginate is a biocompatible hydrogel that can be made in a wide variety of concentrations. It is known that concentrations of about 1.0 to 4.0% can successfully encapsulate mammalian cells, including hepatocytes. Calcium alginate is made from sodium alginate, a water soluble liquid precursor, that has been exposed to calcium chloride.

Chitosan acetate may be used in a wide variety of concentrations mixed with phosphate-free tissue culture media or saline solutions. When the solution is mixed with tripolyphosphate solution, a biocompatible hydrogel is formed.

Polyacrylamides are well-known for their ability to form electrophoresis gels. This gelling ability also makes them well-suited for flow restrictor applications such as those of the present invention.

Figure 2:
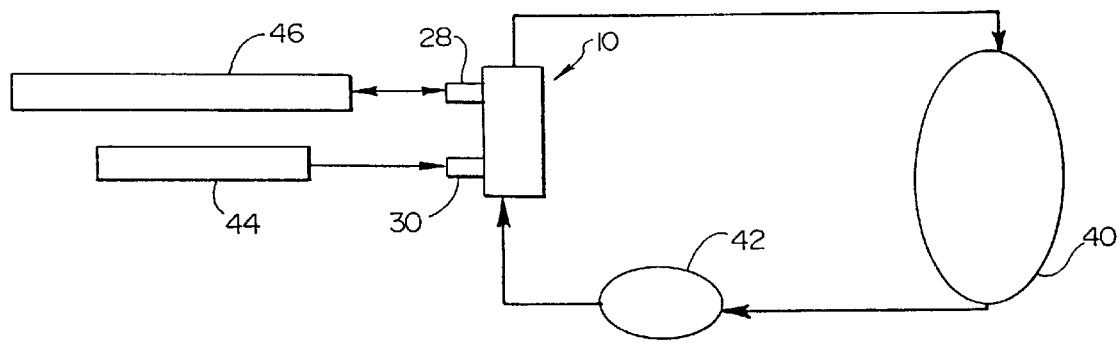
FIG. 2 is a schematic representation of one embodiment of a method for positioning a flow restrictor in a bioreactor.

The flow restrictor may be formed in situ using a variety of methods. In one method, depicted in FIG. 2, the gellable material forming the plug is introduced and positioned by simply injecting it into the housing at the desired location. In FIG. 2, the bioreactor 10 is placed in a fluid circuit with a reservoir 40 of a sterile fluid medium, such as sterile water or Williams' E medium (available from Gibco, Grand Island, N.Y.), and a pump 42. Pressure vent means 46 is provided attached to the housing inlet port 28. The circuit allows the sterile fluid to be circulated through the filament flow path of the bioreactor 10 during formation of the flow restrictor. A syringe pump 44 containing a gellable material in its fluid precursor form is placed in fluid communication with the housing outlet port 30 of the bioreactor. The syringe pump contains a volume of gellable material that, upon gelling, will form a flow restrictor of the desired dimensions at least adjacent to the housing outlet port 30. Upon activation of the syringe pump, the gellable material is caused to enter the housing through the housing outlet port 30, and flow downward, by gravity, to form a liquid slug in the extrafilament space adjacent to the housing outlet port. The liquid slug is then gelled to form the flow restrictor.

Prior to, during or subsequent to the introduction of the gellable material into the housing, the sterile fluid can be circulated through the filament flow path. Such circulation can be used to rinse undesirable substances from the fibers, such as glycerin or isopropyl myristate prior to formation of the hydrogel plug in the extrafilament space. Additionally, if the gelling is carried out by altering the temperature of the gellable material, the temperature of the sterile fluid in the filament flow path circuit can be controlled to activate and regulate the gelling process.

A detailed description of one embodiment of the process is provided in Example 1. Additionally, while it is noted that Example 1 relates to the formation of a collagen plug, it should be understood that the process is intended to have applicability to the formation of other hydrogel plugs. Thus, plugs comprising alginate, chitosan, polyacrylamides, and other two part hydrogels are contemplated as well. For example, in the case of alginate, a sodium alginate solution could be substituted for the collagen solution and additional calcium chloride would be added to the Williams' E medium. Thus, in one embodiment, the hydrogel is intended to be any hydrogel that can be formed by introducing a gellable polymer into the extrafilament space and circulating a gelling catalyst through the filament flow path. Of course, in such a system, the gellable polymer must be incapable of passing through the filament walls, whereas the catalyst must have that ability.

Figure 3A:
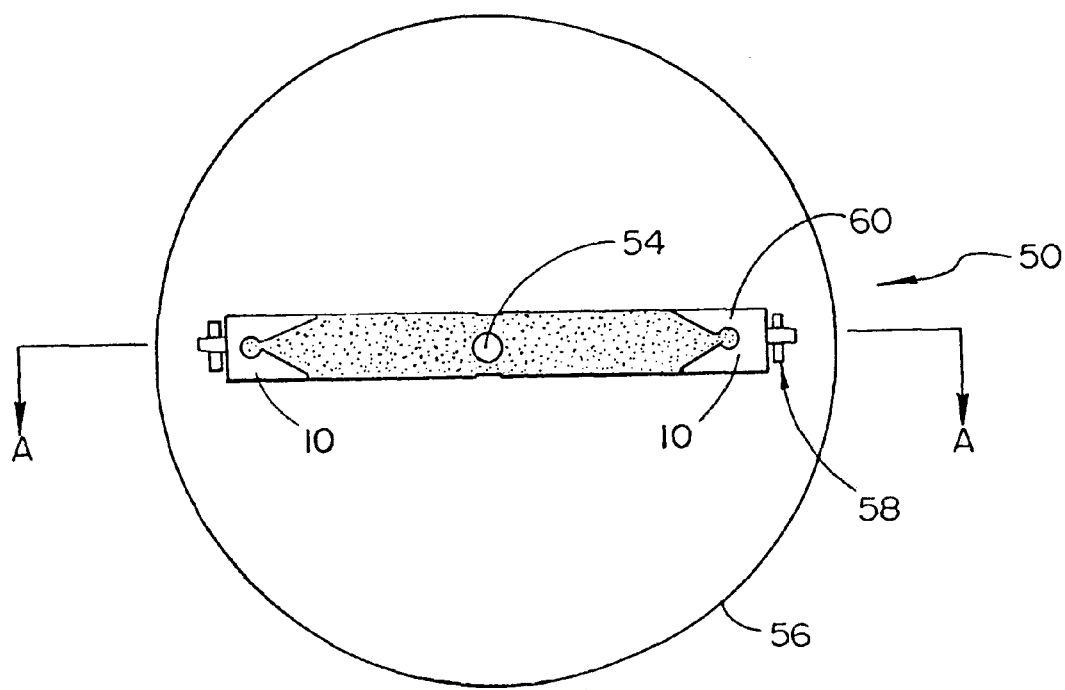
FIGS. 3A and 3B are a schematic representations of a second embodiment of a method for positioning a flow restrictor in a bioreactor.
Figure 3B:
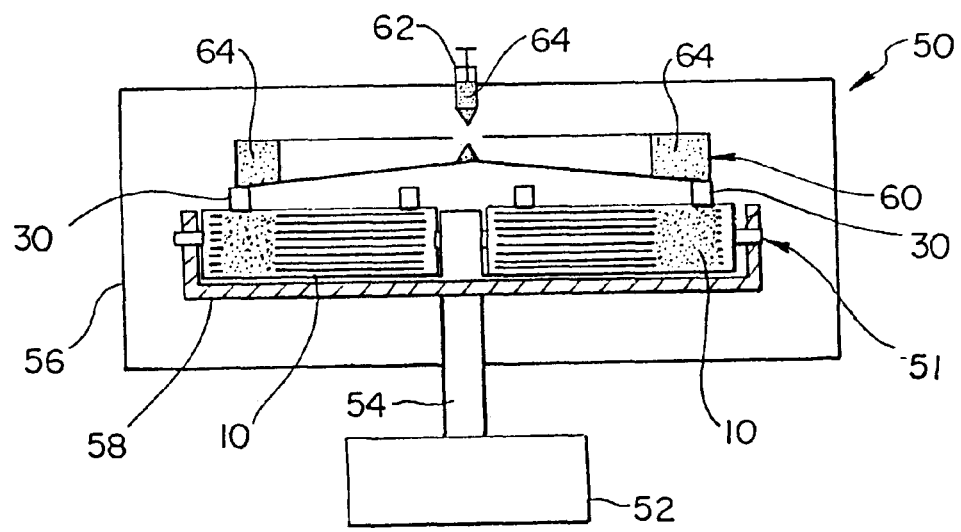

As an alternative, the gellable material may be positioned in the bioreactor using centrifugation. In this method, depicted in FIGS. 3A and 3B, a plurality of bioreactors 10 are positioned within a centrifuge 50. Prior to placement in the centrifuge, the intrafilament space is pressurized to 200 to 300 mmHg and the intrafilament access ports are sealed using lumen pressure retaining caps 51, to allow the intrafilament space to remain pressurized during hydrogel injection. This prevents the hydrogel, in its liquid state, from crossing the filament walls into the filament lumens before the hydrogel has an opportunity to gel. The centrifuge 50 is depicted generally as having a drive motor 52, a rotating shaft 54, and a basket 56. A nest 58, which is rotated by the shaft 54, is used to hold the bioreactors. Positioned above the nest 58 is a potting boat 60 which is in fluid communication with the bioreactors through their housing outlet ports 30. An injector 62 is used to inject the gellable material 64 into the potting boat 60 from which it then enters the bioreactors. In use, the centrifuge is activated, causing the nest, and attached bioreactors, to rotate at approximately 250 to 500 revolutions per minute. Since the lengths, diameters, and filament packing densities will vary among the numerous bioreactor configurations that are envisioned, some experimentation may be required to find an optimum rotation speed for each bioreactor type and each hydrogel precursor. The gellable material 64 is injected into the rotating potting boat from the injector. Due to the rotation, the gellable material is caused to flow outwardly from the middle of the potting boat toward its ends. The gellable material then exits the potting boat and enters the extrafilament space of the bioreactors through the housing outlet port on each. Again, as a result of the rotation, the gellable material is caused to move outwardly, thereby filling the ends of the bioreactors adjacent to the housing outlet ports. In this method, the hydrogel formation should occur as a result of a temperature change, such as by injecting hot agarose and allowing it to cool and set before stopping the centrifuge, or by using a hydrogel that has been precatalyzed, yet has a pregelling time, such as a polyacrylamide. The use of centrifugation is particularly desired in circumstances where the viscosity of the gellable material is so high as to prevent gravity from adequately positioning the material as in FIG. 2.

Once the plug has been formed, the bioreactor is in condition for the insertion of the living cells and, if necessary, their supporting matrix. In one preferred embodiment, the living cells comprise living mammalian cells, such as hepatocytes. The cells preferably are introduced into the bioreactor at a loading density of at least about $10^7$ cells per milliliter, more preferably at a loading density of at least about $10^8$ cells per milliliter. Although not necessary, the cells may be maintained or encapsulated within a gel matrix such as a collagen matrix or the like. In such a case, the cell-supporting matrix may be, but need not be, of the same gel used to form the flow restrictor. It should be noted that although the use of hepatocytes is described in detail throughout, the present invention is not intended to be limited to use with that specific cell type. Rather, any of a wide variety of cells, both primary and transformed, may be used in the present system including, but not limited to, hybridomas, chinese hamster ovary (CHO) cells, baby hamster kidney (BHK) cells, endothelial cells, epithelial cells, and fibroblasts.

Figure 4:
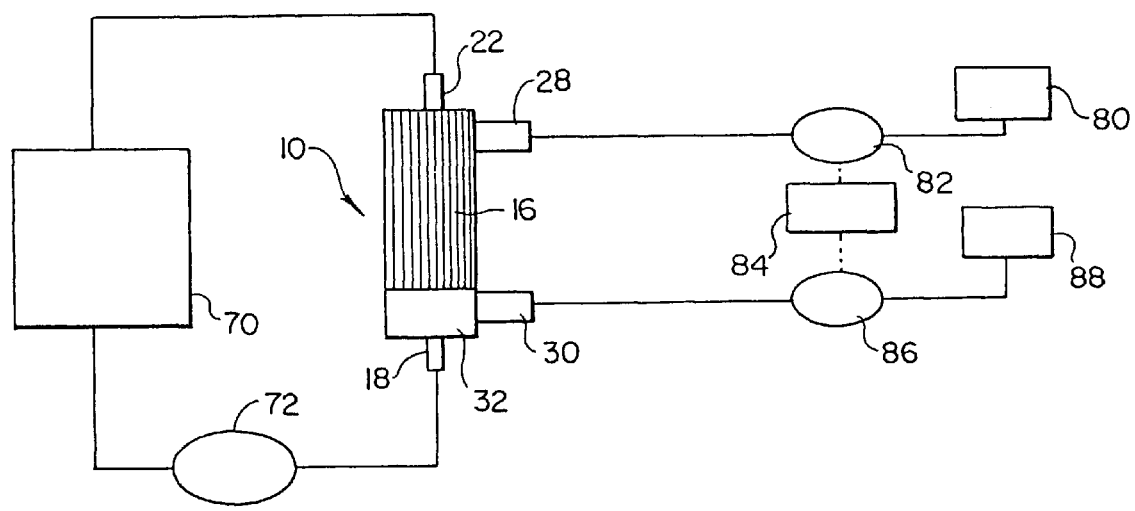
FIG. 4 is a schematic representation of a method for loading a bioreactor with living cells.

In one preferred embodiment depicted in FIG. 4, living cells are introduced into the bioreactor using a method similar to that used to position the flow restrictor. More particularly, the bioreactor 10 is placed in a fluid circuit with a reservoir 70 of a cold, sterile fluid medium, such as William's E medium, and a pump 72. The circuit allows the cold, sterile fluid to be circulated through the filament flow path of the bioreactor 10 during introduction of cells into the bioreactor. Similar to the procedure shown in FIG. 2, the cold, sterile fluid can be circulated from the reservoir 70 by pump 72 into the filament inlet port 18, along the filament flow path, out the filament outlet port 22 and back to the reservoir. The primary purpose of these steps is to keep the bioreactor cold (approx. 4 to 10° C.) while the cells are being loaded. Alternatively, the cell loading operation can be conducted in a controlled, chilled environment, such as in a refrigerator or a cold room.

While circulation of the cold, sterile fluid through the filament flow path is proceeding, the extrafilament space is loaded with cells and, if necessary, a cell-supporting matrix as follows. A reservoir 80 containing the cells is provided. The reservoir is preferably chilled to help maintain cell viability. The solution is transferred from the reservoir 80 by a pump 82 driven by a motor 84. The cell-containing solution enters the bioreactor 10 through the housing inlet port 28. The solution then fills the extrafilament space. As more solution is pumped into the bioreactor, a portion of the solution, is caused to pass through the flow restrictor 32 and the housing outlet port 30. The flow restrictor preferably acts as a filter to trap cells and prevent them from exiting the extrafilament space, while allowing the fluid being displaced by the cells to exit. To assist in the loading process, by reducing pressure pulses and differential pressures across the plug, a second pump head 86 connected to the same motor 84 can be used to simultaneously withdraw the same volume of fluid as the volume of cells being pumped into the extrafilament space of the bioreactor. Fluid exiting the bioreactor is channeled into a waste receptacle 88.

Because the flow restrictor 32 is a hydrogel, it should be apparent that it will impede fluid flow therethrough and causes the significant pressure drop across the restriction. This restriction also causes an increase of the pressure in the extrafilament space which contributes to plug-flow conditions through that space. As a result of the plug-flow conditions, the cell-containing solution is caused to uniformly disperse throughout the extrafilament space, and uniformly distribute cells therethrough. As a result, shunt flow is avoided, and a dense, uniform cell-loading is caused to occur. For determining how much of the cell-containing solution to use, in one preferred embodiment, the amount is determined to be the volume of the extrafilament space less the volume of the flow restrictor. Thus, in a reactor in which the extrafilament space has a volume of about 140 ml and the restrictor occupies a volume of about 40 ml, 100 ml of the cell-containing solution would be used.

If the cells used in the present invention are freshly isolated hepatocytes, a period of 16 to 24 hours of culture is preferably provided to allow the hepatocytes to recover from the trauma of the enzymatic digestion of the liver. Rather than causing the cells to multiply and fill the extrafilament space, however, the purpose of the culture phase as used in the present invention is to allow the cells to recover while establishing natural physiologic-like conditions of pH, temperature and media composition to allow the cells to remain alive and productive.

The resulting, cell-loaded bioreactor offers numerous uses. For example, if the cells are hepatocytes, the bioreactor may be used to sustain a patient undergoing full or partial liver failure until liver function returns or a suitable transplant can be provided. The bioreactor acts as an artificial liver and purifies the blood.

Once the cells have been loaded into the bioreactor, the bioreactor can be placed into any of several types of culture circuits. Examples of such culture circuits are described in U.S. Pat. No. 3,883,393 (Knazek), U.S. Pat. No. 4,220,725 (Knazek), and U.S. Pat. No. 4,804,628 (Cracauer). If the cells have been genetically altered to secrete a biologic product, it is possible, using the present invention, to begin harvesting cell secreted product almost immediately. This may be contrasted with conventional systems in which it is often necessary to wait days or weeks for the cells to undergo multiple divisions and fill the reactor prior to secreting useful amounts of biologic products.

Figure 5:
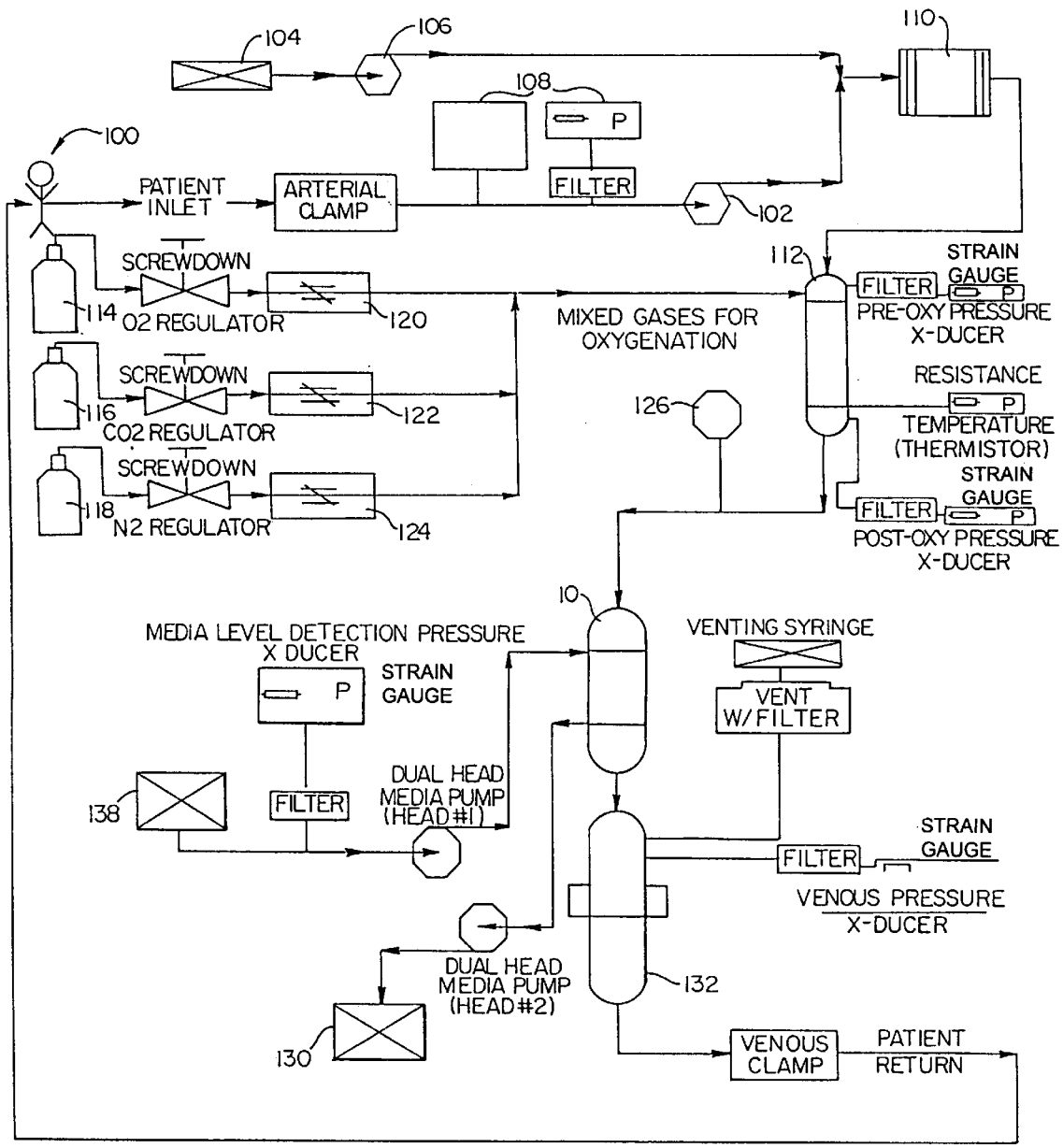
FIG. 5 is a schematic representation of a method of use of the bioreactor of the present invention.

A system in which the bioreactor contains hepatocyes and is used to purify blood is depicted schematically in FIG. 5. In FIG. 5, blood from a patient 100 is pumped by a blood pump 102 and mixed with heparin 104 which has been pumped by a heparin pump 106. Pressure monitoring apparatus 108 is a safety device. If a problem occurs with the patient, the patient's blood access site, or the tubing leading from the patient, an increase in negative pressure will be detected and can be used to activate an alarm. The heparinized blood is then heated in a blood warmer 110 to a desired temperature and the introduced into an oxygenator 112. The oxygenator 112 is provided with sources of oxygen 114, carbon dioxide 116 and nitrogen 118 each regulated by a flow controller (120, 122 and 124, respectively) so that a desired blood gas content and blood pH can be achieved and maintained. The oxygenator includes pressure and temperature monitoring equipment, and other blood handling subsystems commonly used in the art. The oxygenated blood is monitored by a pH probe 126 and then passed through the filament flow path of the bioreactor 10. As the blood passes through the filament flow path, numerous impurities of the type normally removed by the liver are caused to diffuse through the filament walls to the hepatocytes. The hepatocytes provide liver function of the type normally occurring in vivo to the blood. During this process, the hepatocytes can be maintained by a nutrient medium which travels through the extrafilament flow path. The nutrient medium is provided by a media supply reservoir 138 which includes pressure monitoring subsystems to determine the amount of nutrient remaining in the nutrient reservoir. Spent nutrient media exits the bioreactor and travels to a media waste receptacle 130. It should be noted, however, that the use of a circulating nutrient solution, particularly during treatment of a patient, is entirely optional, and need not be performed. Treated blood exiting the bioreactor is passed through an air/foam detector 132 and then back to the patient.

It is believed that systems of the type described and depicted in FIG. 5 may be used to maintain patients undergoing partial or full liver failure for up to until a suitable donor liver can be found or until the patient's liver recovers acceptable function. In this latter case, several intermittent treatments over the course of several days or weeks may be required. This offers the benefit of providing sufficient time for the patient's liver to return to normal function or to locate a donor organ sufficient for transplantation. Of course, it should be noted that the bioreactors of the present invention are not intended to be limited strictly to liver function, but rather, that such reactors may be suitable for a broad range of clinical applications in which it is desirable to provide extracorporeal systems for maintaining living cells at densities and functionalities approaching those of normal animal tissue.

EXAMPLES

Example 1
Formation of a Collagen Hydrogel Plug in a Hepatocyte Bioreactor

In this example, reference numerals refer to the reference numeral of the Figures, particularly FIGS. 1 and 2.

One liter of filter sterilized Williams' E medium, pH 7.40, at 4° C. was introduced into a reservoir 40. Sterile tubing was used to connect the reservoir to a pump 42 and from the pump to one filament port of the bioreactor. Additional sterile tubing was connected from the other filament port of the bioreactor to a temporary sterile waste receptacle. Approximately 45 ml of sterile Vitrogen-100 was drawn into a sterile 60 ml syringe, and the syringe was connected, via sterile tubing to the housing inlet port 28. A sterile hydrophobic air filter and sphygmomanometer was connected to the housing outlet port 30. The sphygmomanometer was arranged to communicate with the extrafilament space through the filter in order to maintain sterility of the bioreactor.

The extrafilament space was pressurized to approximately 200 to 300 mmHg pressure, and the pump 42 was started. Approximately 500 ml of Williams' E medium was allowed to flow through the bioreactor and into the sterile waste receptacle before further steps were carried out. This was done in order to rinse the filaments and to remove any glycerin or other unwanted contaminants from their interior. The pump was then stopped and the outlet tube from the reactor was clamped and transferred from the sterile waste receptacle to the reservoir 40. The extrafilament space was then depressurized and maintained at ambient atmospheric pressure.

The collagen-filled syringe was then positioned in a syringe pump 44, and about 40 ml of Vitrogen-100 was pumped into the extrafilament space of the bioreactor. The collagen was pumped into the bioreactor at a rate of about 40 ml per hour. Once the collagen had been pumped into the bioreactor, the tube connecting the syringe to the extrafilament inlet port was clamped off. The other extrafilament port was closed off as well, by closing the needle valve on the sphygmomanometer. The intralumenal outlet tubing was unclamped and the intralumenal circulation pump was turned on at a flow rate of approximately 30 ml per minute.

As Williams' E medium (pH 7.4) flowed through the filaments, the pH of the collagen in the extrafilament space was caused to rise from about 2.0 to neutral. In so doing, the collagen was caused to gel. During the initial phase of the gelling, the pressure in the extrafilament flow path was closely controlled, by adjustment of the sphygmomanometer needle valve. The close control was required to prevent ultrafiltration, a condition in which media can cross from the filament flow path into the extrafilament space through the filament walls. This condition is undesirable as it dilutes and changes the volume of the hydrogel solution in the extrafilament space. This was accomplished by carefully observing the level of the collagen solution in the extrafilament space and adjusting the pressure in that space as described above. Although not wishing to be bound by any particular theory, it is believed that the pressure rises primarily as a result of $CO_2$ gas that evolves as hydrochloric acid in the collagen solution is neutralized by sodium bicarbonate resident in the Williams' E medium.

After the Williams' E medium was circulated at a rate of about 30 ml/min for approximately 30 to 45 minutes, the rate of the intrafilament circulation pump was doubled to about 60 ml/min for about 30 minutes, and the reservoir 40 was placed in a 37° C. water bath. The rate of the intrafilament circulation pump was doubled every 30 minutes until a flow rate of about 240 ml/min was achieved. At that point, gellation of the collagen was substantially complete. The remainder of the extrafilament space, not occupied by the collagen plug, was allowed to fill, via ultrafiltration, with Williams' E medium by venting the extrafilament space until the medium reached the hydrophobic air filter. The medium was then allowed to circulate for several hours to ensure that the collagen plug was fully set, and to neutralize any residual hydrochloric acid.

Example 2
Hepatocyte Harvest and Isolation

Porcine hepatocytes were harvested from 7 to 12 kg male pigs (Midwest Research Swine, Gibbon, Minn.) using a two step collagenase technique. The animals were anesthetized with ketamine intramuscularly, intubated, and sterilely prepared and draped. A midline incision was used to enter the abdomen. The infrahepatic inferior vena cava (IVC) and suprahepatic IVC above the diaphragm were isolated and encircled. The protal triad was then dissected, ligated and all structures were divided except the hepatic artery and the portal vein, which were isolated and looped. Heparin, at 300 I.U. per kg, was given. After 3 minutes, the cannula, connected by sterile silicone tubing to a peristaltic pump, was passed into the surgical field. The hepatic artery was then ligated and divided, and the portal vein was cannulated. Five liters of PER-I solution (calcium-free hydroxyethylpiperazine-ethanesulfonic acid (HEPES) buffered solution (143 mM NaCl, 6.7 mM KCl, 10 mM HEPES, 100 mg % ethylene glycol-bis-aminoethyl ether (EGTA), pH 7.4), at a rate of 1 liter per kg body weight was perfused through a silicone oxygenator and heat exchanger (Avecor Cardiovascular, Minneapolis, Minn.) and then directly into the portal vein to wash out the blood. The suprahepatic IVC was then ligated and divided, and the infrahepatic IVC was divided to allow outflow of the perfusate. During the initial perfusion, the liver was transferred to a sterile tray. Two liters of PER II (HEPES buffered solution (67 mM NaCl, 6.7 mM KCl, 4.8 mM $CaCl_2$, 100 mM HEPES, pH 7.6), 1 gm/liter Collagenase-D (Boehringer Mannheim, Indianapolis, Ind.)) was then recirculated through the liver, at the same flow rate as the PER-I, for 10 to 15 minutes until the liver was soft and well digested, as determined by palpation and visual inspection.

The liver was removed to a laminar flow hood and the capsule was incised on all lobes. Next, the liver was skeletonized bluntly with gentle agitation in 5° C. Williams'-E medium to free the hepatocytes. The cell laden media was filtered through a Buchner funnel which contained a single layer of sterile gauze to remove any tissue fragments, into sterile 250 ml centrifuge tubes which were spun at 500 to 700 RPM for 5 minutes to form a soft cell pellet. The pellet was resuspended in fresh medium and centrifuged two more times. Hepatocyte viability and cell number was assessed by using a hemocytometer and Trypan Blue dye exclusion methods.

Example 3
Bioreactor Loading

Approximately 100 ml of hepatocyte cell pellet was transferred to a sterile 250 ml polyethylene bottle. 25 ml of Vitrogen-100 was added to the cells and the bottle was gently swirled to mix the collagen and cells. 100 ml of this solution was pipetted, 50 ml into each of two 60 cc syringes (Becton Dickinson, Franklin Lakes, N.J.) and connected to a circuit similar to the one shown in FIG. 4. The syringes were placed on ice to keep the cells cool. The cell loading pump 84 was set to a rate of 100 ml/hr to inject the cells into the extrafilament space over a one hour period. The intrafilament pump 72 was set to a flow rate of 300 ml/min to keep the bioreactor cool during cell loading. After all of the hepatocyte solution was pumped into the extrafilament space, sterile caps were placed on all of the ports and the bioreactor was transferred to an incubator in which $CO_2$ and humidity were controlled.

Example 4
Bioreactor Culture

Figure 6:
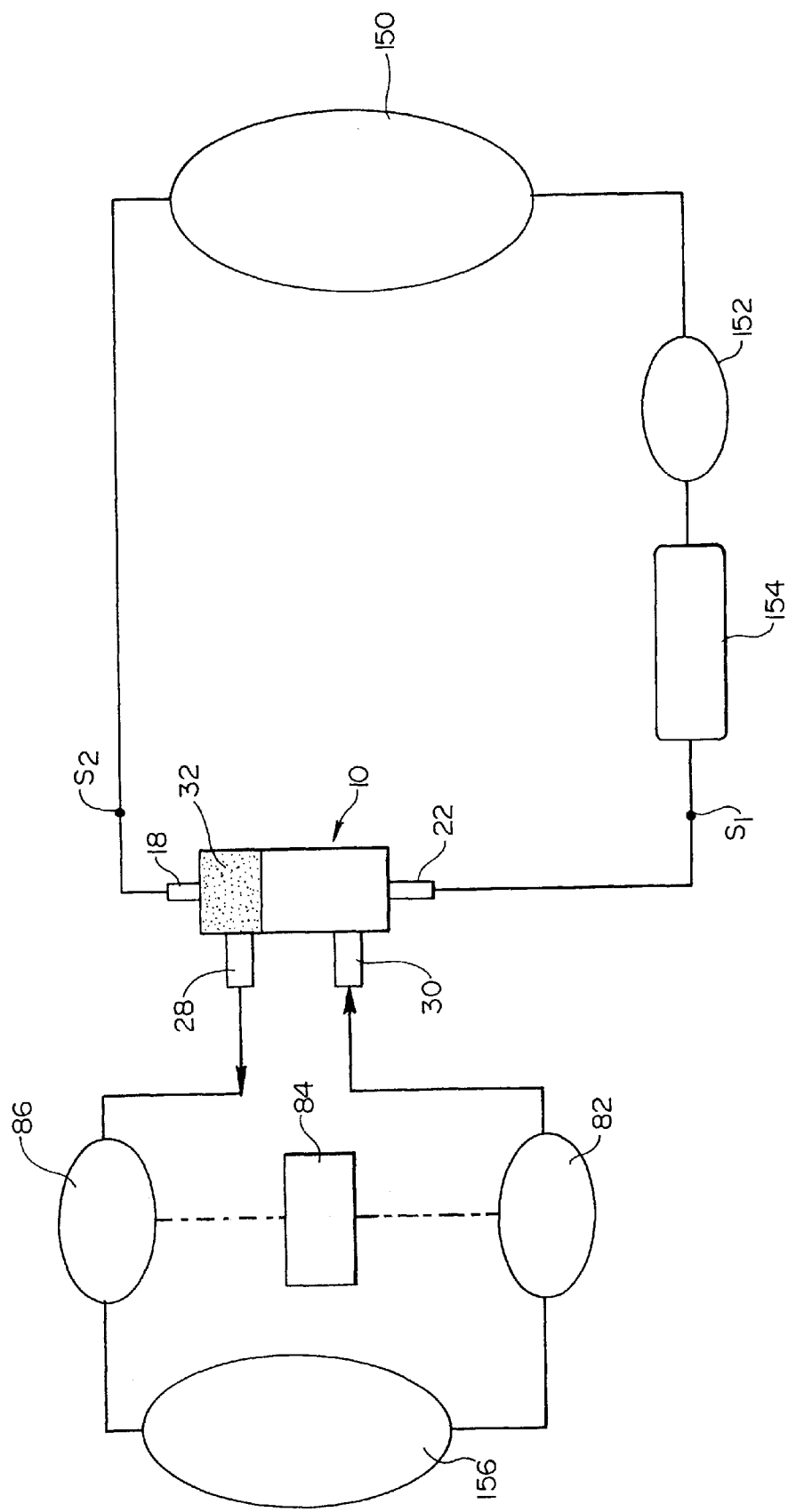
FIG. 6 is a schematic representation of a method for maintaining a bioreactor loaded with living cells during a culture phase.

An example of the fluid circuits employed during the culturing phase of the bioreactor manufacture is depicted schematically in FIG. 6. The hepatocyte containing bioreactor was placed in the culture circuit and maintained for approximately 18 hours in the incubator to allow the cells to rest. During this time the cells can recover from the stress of harvest and re-establish cell to cell contact and remodel their local environment.

The incubator $CO_2$ was maintained at 5.5%, temperature at 37° C. and the humidity at 70–80%. The bioreactor was maintained in a circuit of the type shown in FIG. 6. The intrafilament circuit was comprised of a 1 liter reservoir 150 containing Williams'-E medium formulated as shown in Table 1:

TABLE 1

| Intrafilament Medium | | |
|---|---|---|
| Component | Amount per liter | Source/Quality |
| Wm's-E Powder with Glutamine | 10.79 g | Life Technologies |
| Sodium Bicarbonate | 2.2 grams | Sigma Chemical |
| Penicillin | 40,000 Units | Life Technologies |
| Streptomycin | 400 mg | Life Technologies |
| Transferrin | 6.25 mg | Sigma |
| Epidermal Growth Factor | 5.05 ug | Sigma |
| Insulin | 4 mg/111.8 IU | Sigma |
| Glucagon | 0.4 mg | Sigma |
| Selenium | 2.854 ug | Sigma |
| Dexamethasone | 3.295 ug | Sigma |

A peristaltic pump 152 operating at 700–900 ml/min was used to pump media from the 1 liter reservoir 150 through a silicone membrane oxygenator 154, where the media is oxygenated and pH adjusted to 7.2. Oxygenation and pH control via the oxygenator was achieved by using an air pump (MEDO U.S.A., Hanover Park, Ill.) (not shown) to circulate the incubator gasses through the gas path of the oxygenator. From the oxygenator 154, the media was delivered into the intraluminal space of the bioreactor 10, and then returned to the 1 liter reservoir 150 from the outlet 18 of the intraluminal space of the bioreactor. Sample points $S_1$ and $S_2$ were used to periodically withdraw media, before and after the bioreactor, for blood gas analysis of pH and oxygen content. Recirculation was maintained until the bioreactor was removed for connection to a liver injured dog.

On the extrafilament side of the bioreactor was a second circulation path which included a 500 ml reservoir 156 of media formulated as shown in Table 2:

TABLE 2

| Extrafilament Medium | | |
|---|---|---|
| Component | Amount per liter | Source/Quality |
| Wm's-E Powder with Glutamine | 10.79 g | Life Technologies |
| Sodium Bicarbonate | 2.2 g | Sigma Chemical |
| Penicillin | 40000 Units | Life Technologies |
| Streptomycin | 40 mg | Life Technologies |
| Bovine Serum Albumin-10% linoleic acid | 500 mg (HSA) | Sigma |
| Transferrin | 6.25 mg | Sigma |
| Epidermal Growth Factor | 5.05 ug | Sigma |
| Insulin | 4 mg/111.8 IU | Sigma |
| Glucagon | 0.4 mg | Sigma |
| Selenium | 2.854 ug | Sigma |
| Dexamethasone | 329.5 ug | Sigma |

Circulation of the extrafilament media was not started until 12 hours after the bioreactor had been installed in the incubator. The circulation rate was 30 ml/hour and was continued until the bioreactor was removed for use on the liver injured dog.

Example 5
Canine Liver Injury and Bioreactor Treatment

Evaluation of the hepatocyte-containing bioreactor for use as a bioartificial liver was conducted using a lethal canine galactosamine liver failure model similar to that described by Sielaff et al. (*Hepatology,* 21:(3), 1995). Modifications from the protocol as published by Sielaff included replacement of halothane with isofluorane as the anesthetic and more frequent laboratory testing to manage the animal proactively. In addition, the source animals were purpose-bred, well-conditioned hunter hounds instead of the mongrel animals reported in the Sielaff studies. As a result of these changes, the animals lived somewhat longer than reported and the studies were consequently extended to 60 hours.

Dogs receiving D-galactosamine (1.5 gram/kilogram body weight) were allowed to proceed into liver failure for 24 hours at which point hemoperfusion with the bioartificial liver was initiated. The vascular access device was a dual lumen catheter surgically implanted in the right internal jugular vein prior to administration of the D-galactosamine.

The treatment objective was to hemoperfuse at the highest possible flow rate until the animal expired o r reached the end of the 60 hour study period and was electively euthanized. In practice, initial flow rates typically exceeded 200 ml/min. This rate dropped as the animal became increasingly edematous and the patency of the vascular access deteriorated. In no case was the catheter lost to clotting. In some studies, blood flow rate dropped to less than 100 ml/min 50 hours after drug administration or after 26 hours of continuous hemoperfusion.

Figure 7:
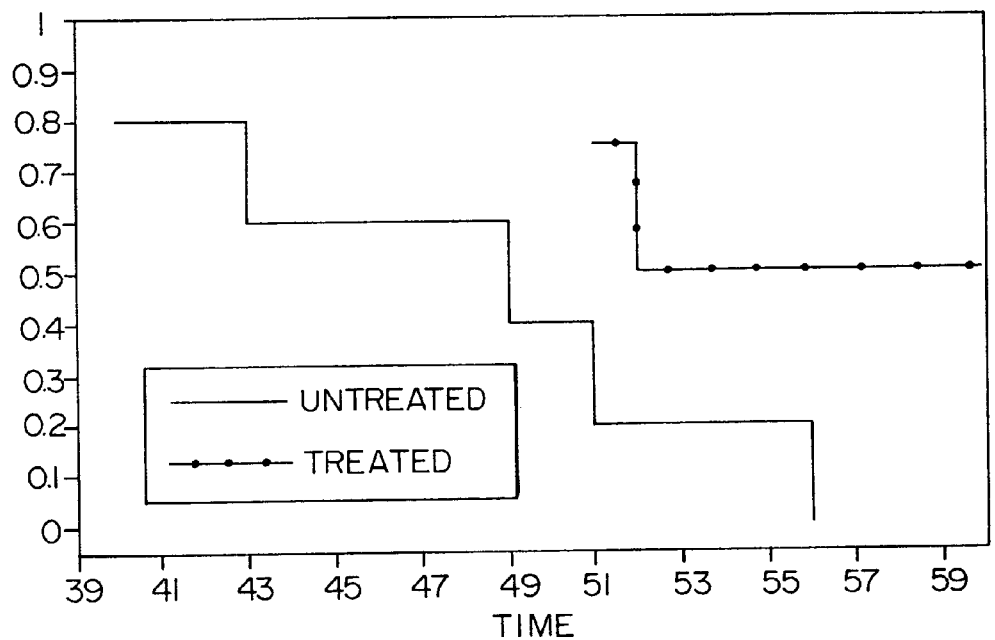
FIG. 7 is a Kaplan-Meier plot showing survival differences in treated and untreated test subjects.

Four animals were treated in this manner with bioreactors charged with 60 to 80 grams of primary porcine hepatocytes. The animals were managed according to the same intervention schedule as the control subjects. Two of the four treated animals survived to the end of the study period. In contrast none of the untreated animals did. The survival difference is shown in the form of the Kaplan-Meier plot of FIG. 7 in which the cumulative proportion surviving is plotted against time.

The five untreated control animals and four treated animals included in the data set were evaluated by the Kaplin-Meier survival statistic. The results do not reach statistical significance (p=0.06) due to sample size and to the arbitrary termination condition for the study.

TABLE 3

Statistical Evaluation

| Variable | Group | | Time |
|---|---|---|---|
| Survival Time | Untreated | mean | 47.8 |
| | | sem | 2.9 |
| | | n | 5 |
| | Treated | mean | 55.8 |
| | | sem | 2.5 |
| | | n | 4 |
| | Statistic | t-test | 0.080 |
| | | Log Rank | 0.065 |
| | | Breslow | 0.064 |
| | | Tarone-Ware | 0.063 |

Figure 8:
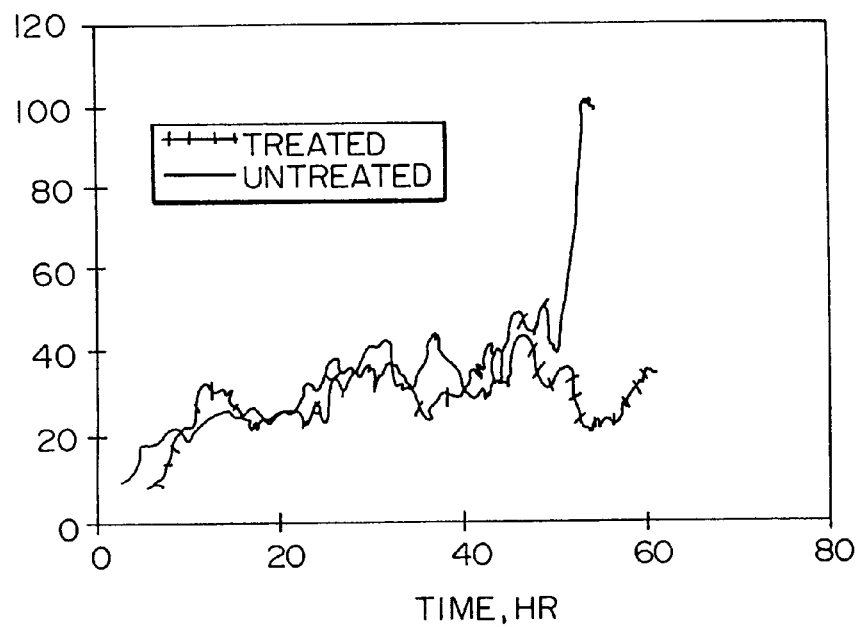
FIG. 8 is a plot showing intracranial pressures vs. time in treated and untreated test subjects.

Animals were fitted with LADD superdural Intracranial pressure monitors. These were monitored continuously throughout the study but data were recorded hourly. The results for each of the four treated animals are shown in FIG. 8 along with the mean of these data. The animals supported with the bioartificial liver showed an oscillatory ICP pattern similar to that exhibited by the control animals. As before, the sampling interval chosen obscures the surges in ICP observed by the attending staff.

The average reading of the five control and four treated animals are compared in FIG. 8 in which intracranial pressure is plotted against time. Statistical tests were not applied to these data due to a variety of confounding factors present in the data set. These factors include the fact that more frequent and aggressive medical intervention occurred in the untreated animals (as permitted under the management guidelines), than was evidently necessary with the treated animals. Bias is also introduced because the longer lived untreated animals have on average lower ICP values than those expiring earlier in the study.

Figure 9:
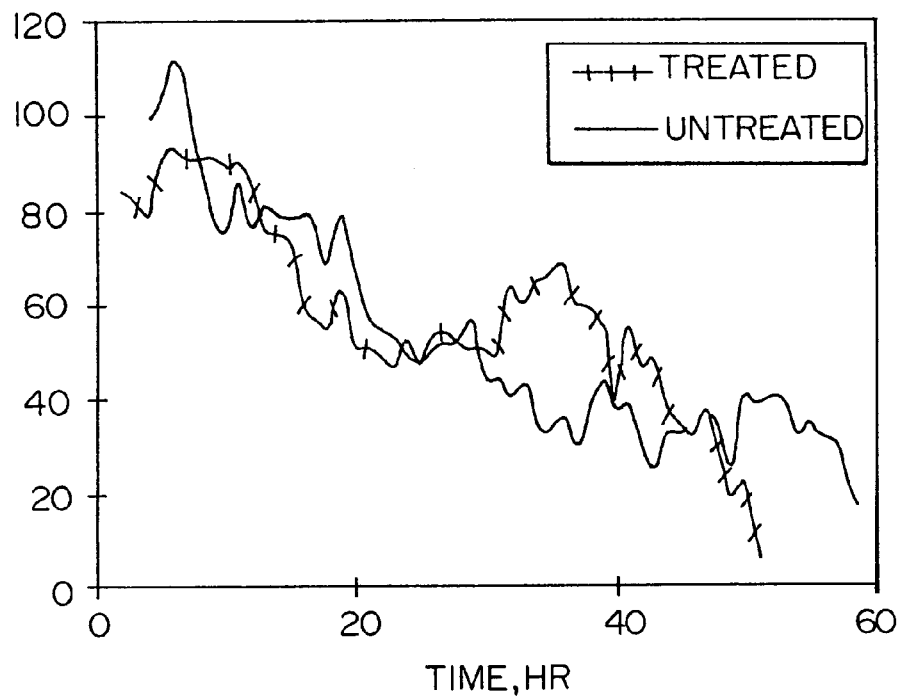
FIG. 9 is a plot showing cerebral perfusion pressures vs. time in treated and untreated test subjects.

With both ICP data and mean arterial pressure (MAP) data available, it is possible to calculate the cerebral perfusion pressure (CPP) in these study animals. As shown in FIG. 9 in which cerebral perfusion pressure is plotted against time, CPP declines in treated animals as it does in the untreated ones. Furthermore, those animals with the lower values appear to have shorter survival times.

The arithmetic means of the CPP values for treated and untreated dogs are plotted together in FIG. 9. Decreasing blood flow to the brain is present in both groups of animals. The rise in CPP in the untreated animals between 30 and 40 hours after administration of the drug may be due to more aggressive intervention to correct falling blood pressure in the untreated population.

Figure 10:
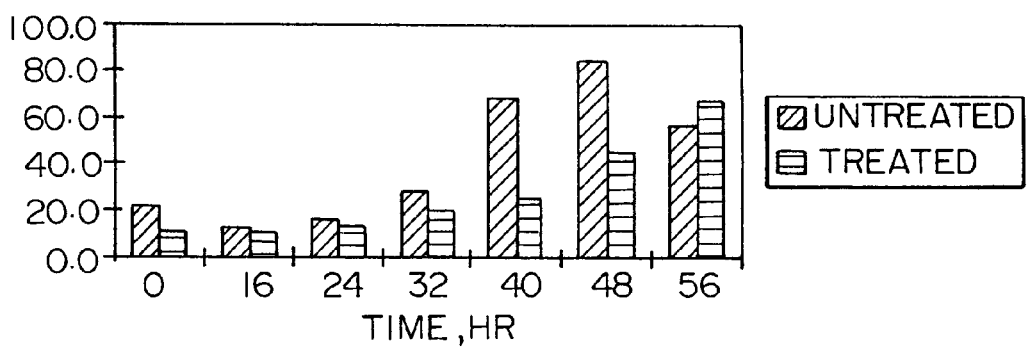
FIG. 10 is a plot showing ammonia levels in treated and untreated test subjects.

As shown in FIG. 10 in which ammonia levels are plotted against time, the rise in arterial ammonia levels is moderated in treated animals. The effect is not statistically significant at 40 and 48 hours, because of the large dispersion in the data from the untreated animals. The convergence of data at 56 hours is a result of the fact that the sicker untreated animals, those with higher values of ammonia, have shorter survival times.

Figure 11:
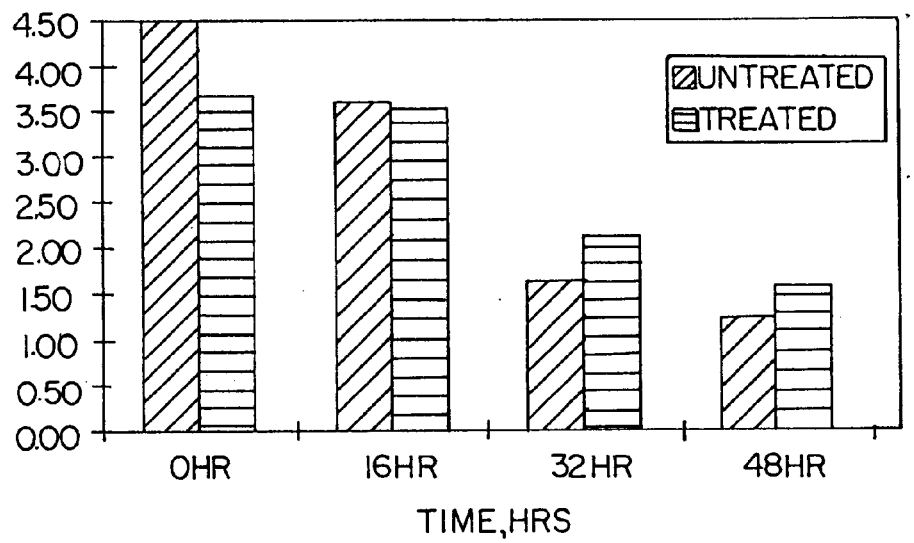
FIG. 11 is a plot showing the ratio of branched amino acid levels to aromatic amino acid levels in treated and untreated test subjects.
Figure 12:
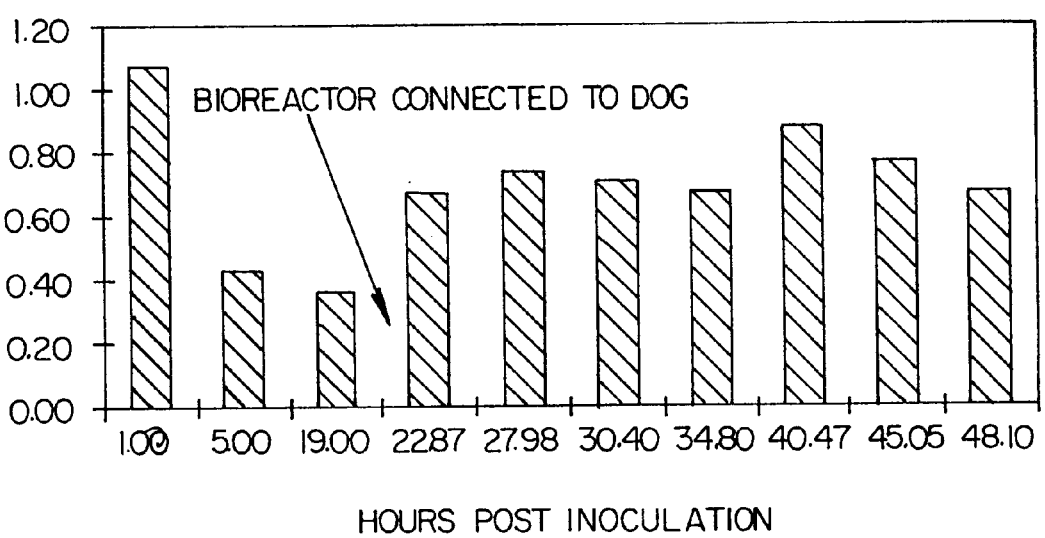
FIG. 12 is a plot showing in vivo oxygen consumption rates for the bioreactors of the present invention.

The ratio of branched chain amino acids (BCAA) and aromatic amino acids (AAA) declines in both treated and untreated animals, as shown in FIG. 11, in which the BCAA/AAA ratio is plotted against time. The difference reaches statistical significance at 48 hours. Intermediate values were not obtained and it is not clear if the magnitude of this change is sufficient to generate a meaningful patient benefit. The rate of oxygen consumption in the bioreactor before and after connection to a dog is shown in FIG. 12, in which the bioreactor oxygen consumption rate is plotted against hours after inoculation.

Equivalents

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A bioreactor which comprises:
   a) an elongate housing defining a central axis;
   b) a plurality of elongate hollow filaments each positioned within the housing substantially parallel to the central axis and defining an extrafilamentary space within the housing, each of the hollow filaments formed of a material which allows molecular transport therethrough;
   c) a cell population positioned within the housing, the cell population occupying the extrafilamentary space and comprising living cells;
   d) a filament inlet port and a filament outlet port, said ports communicating through the hollow filaments to define a filament flow path;
   e) a housing inlet port and a housing outlet port, said ports communicating through the cell population to define an extrafilament flow path, the extrafilament flow path being isolated from the filament flow path such that a material in one path may enter the other path only by molecular transport through the material comprising the hollow filaments; and
   f) a plug positioned in the extrafilament flow path to maintain a substantially uniform flow across the extrafilament flow path.

2. A bioreactor of claim 1 wherein the cells are mammalian cells.

3. A bioreactor of claim 2 wherein the cells are hepatocytes.

4. A bioreactor of claim 1 wherein the cells are present at a density of at least about $10^7$ cells per milliliter.

5. A bioreactor of claim 4 wherein the cells are hepatocytes.

6. A bioreactor of claim 1 wherein the cells are present at a density of at least about $10^8$ cells per milliliter.

7. A bioreactor of claim 6 wherein the cells are hepatocytes.

8. A bioreactor of claim 1 wherein the plug comprises a hydrogel.

9. A bioreactor of claim 1 wherein the plug comprises a material selected from collagen, agarose, calcium alginate, chitosan acetate, a polyacrylamide, or a combination thereof.

10. A bioreactor of claim 1 wherein the filaments are selected from filaments made of polysulfone, cellulose acetate, polyacrylonitrile, polymethylmethacrylate, or an ethylene polyvinyl alcohol copolymer.

11. An extracorporeal circuit comprising the bioreactor of claim 1.

12. An extracorporeal circuit of claim 11 wherein the cells are hepatocytes.

13. A method for treating a biological fluid which comprises:
   a) providing a bioreactor which comprises
      i) an elongate housing defining a central axis;
      ii) a plurality of elongate hollow filaments each positioned within the housing substantially parallel to the central axis and defining an extrafilamentary space within the housing, each of the hollow filaments formed of a material which allows molecular transport therethrough;

iii) a cell population positioned within the housing, the cell population occupying the extrafilamentary space and comprising living cells capable of treating the biological fluid;

iv) a filament inlet port and a filament outlet port, said ports communicating through the hollow filaments to define a filament flow path;

v) a housing inlet port and a housing outlet port, said ports communicating through the cell population to define an extrafilament flow path, the extrafilament flow path being isolated from the filament flow path such that a material in one path may enter the other path only by molecular transport through the material comprising the hollow filaments; and vi) a plug positioned in the extrafilament flow path to maintain a substantially uniform flow across the extrafilament flow path; and b) causing the biological fluid to travel along the filament flow path.

14. The method of claim 13 which further comprises causing a fluid containing nutrients for the cells to travel along the extrafilament flow path.

15. The method of claim 14 wherein the filament flow path and the extrafilament flow path have co-current flow.

16. The method of claim 14 wherein the filament flow path and the extrafilament flow path have counter-current flow.

17. The method of claim 13 wherein the cells are mammalian cells.

18. The method of claim 17 wherein the cells are hepatocytes.

19. The method of claim 18 wherein the biological fluid comprises blood.

20. The method of claim 13 wherein the cells are present at a density of at least about $10^7$ cells per milliliter.

21. The method of claim 20 wherein the cells are hepatocytes.

22. The method of claim 13 wherein the cells are present at a density of at least about $10^8$ cells per milliliter.

23. The method of claim 22 wherein the cells are hepatocytes.

24. The method of claim 13 wherein the plug comprises a hydrogel.

25. The method of claim 13 wherein the plug comprises a material selected from collagen, agarose, calcium alginate, chitosan acetate, a polyacrylamide, or a combination thereof.

26. The method of claim 13 wherein the filaments are selected from filaments made of polysulfone, cellulose acetate, polyacrylonitrile, polymethylmethacrylate, or an ethylene polyvinyl alcohol copolymer.

27. The method of claim 13 wherein the biological fluid comprises blood.

28. A method of fabricating a bioreactor having a plug, the method comprising:

a) providing a hollow filament bioreactor cartridge, the cartridge comprising a housing containing a plurality of elongate hollow filaments each positioned within the housing substantially parallel to the central axis and defining an extrafilamentary space within the housing, each of the hollow filaments formed of a material which allows molecular transport therethrough, the housing further comprising a filament inlet port and a filament outlet port, said ports communicating through the hollow filaments to define a filament flow path, and a housing inlet port and a housing outlet port, said ports communicating through the extrafilamentary space to define an extrafilament flow path, the extrafilament flow path being isolated from the filament flow path such that a material in one path may enter the other path only by molecular transport through the material comprising the hollow filaments; and b) introducing a volume of a gellable material into the housing in a manner such that it becomes positioned at least adjacent to the housing outlet port, the volume such that, upon gelling, the resulting gel will form a plug positioned in the extrafilament flow path to maintain a substantially uniform flow across the extrafilament flow path.

29. The method of claim 28 which further comprises gelling the gellable material while flowing a sterile fluid through the filament flow path.

30. The method of claim 29 wherein the gelling is controlled by varying the temperature of the sterile fluid.

31. The method of claim 28 wherein the gelling is controlled by temperature variation.

32. The method of claim 28 wherein the gel becomes positioned at least adjacent to the housing outlet port by gravity.

33. The method of claim 28 wherein the gel becomes positioned at least adjacent to the housing outlet port by centrifugation.

34. The method of claim 28 wherein the gel comprises a material selected from collagen, agarose, calcium alginate, chitosan acetate, a polyacrylamide, or a combination thereof.

35. A bioreactor which comprises:

a) an elongate housing defining a central axis;

b) a plurality of elongate hollow filaments each positioned within the housing substantially parallel to the central axis and defining an extrafilamentary space within the housing, each of the hollow filaments formed of a material which allows molecular transport therethrough;

c) a filament inlet port and a filament outlet port, said ports communicating through the hollow filaments to define a filament flow path;

d) a housing inlet port and a housing outlet port, said ports communicating through the extrafilamentary space to define an extrafilament flow path, the extrafilament flow path being isolated from the filament flow path such that a material in one path may enter the other path only by molecular transport through the material comprising the hollow filaments; and e) a plug positioned in the extrafilament flow path to maintain a substantially uniform flow across the extrafilament flow path, the plug positioned at least adjacent to the housing outlet port.

36. A bioreactor of claim 35 wherein the plug comprises a hydrogel.

37. A bioreactor of claim 35 wherein the plug comprises a material selected from collagen, agarose, calcium alginate, chitosan acetate, a polyacrylamide, or a combination thereof.

38. A bioreactor of claim 34 wherein the filaments are selected from filaments made of polysulfone, cellulose acetate, polyacrylonitrile, polymethylmethacrylate, or an ethylene polyvinyl alcohol copolymer.

39. A bioreactor which comprises:

a) an elongate housing defining a central axis;

b) a plurality of elongate hollow filaments each positioned within the housing substantially parallel to the central axis and defining an extrafilamentary space within the housing, each of the hollow filaments formed of a material which allows molecular transport therethrough;

c) a cell population positioned within the housing, the cell population occupying the extrafilamentary space and comprising living cells;

d) a filament inlet port and a filament outlet port, said ports communicating through the hollow filaments to define a filament flow path;

e) a housing inlet port and a housing outlet port, said ports communicating through the cell population to define an extrafilament flow path, the extrafilament flow path being isolated from the filament flow path such that a material in one path may enter the other path only by molecular transport through the material comprising the hollow filaments; and f) a plug positioned in the extrafilament flow path to maintain a substantially uniform flow across the extrafilament flow path, the plug positioned at least adjacent to the housing outlet port.

40. A bioreactor which comprises:

a) an elongate housing defining a central axis;

b) a plurality of elongate hollow filaments each positioned within the housing substantially parallel to the central axis and defining an extrafilamentary space within the housing, each of the hollow filaments formed of a material which allows molecular transport therethrough;

c) a cell population positioned within the housing, the cell population occupying the extrafilamentary space and comprising living cells;

d) a filament inlet port and a filament outlet port, said ports communicating through the hollow filaments to define a filament flow path;

e) a housing inlet port and a housing outlet port, said ports communicating through the cell population to define an extrafilament flow path, the extrafilament flow path being isolated from the filament flow path such that a material in one path may enter the other path only by molecular transport through the material comprising the hollow filaments; and f) a plug positioned in the extrafilament flow path to maintain a substantially uniform flow across the extrafilament flow path, the plug being configured to prevent the cells from exiting the housing through the housing outlet port.

41. A bioreactor which comprises:

a) an elongate housing defining a central axis;

b) a plurality of elongate hollow filaments each positioned within the housing substantially parallel to the central axis and defining an extrafilamentary space within the housing, each of the hollow filaments formed of a material which allows molecular transport therethrough;

c) a filament inlet port and a filament outlet port, said ports communicating through the hollow filaments to define a filament flow path;

d) a housing inlet port and a housing outlet port, said ports communicating through the extrafilamentary space to define an extrafilament flow path, the extrafilament flow path being isolated from the filament flow path such that a material in one path may enter the other path only by molecular transport through the material comprising the hollow filaments; and e) a plug positioned in the extrafilament flow path to maintain a substantially uniform flow across the extrafilament flow path, the plug being configured to prevent the cells from exiting the housing through the housing outlet port.

42. A method of making a bioreactor having a plug comprising:

a) providing a hollow filament bioreactor cartridge, the cartridge comprising a housing containing a plurality of elongate hollow filaments each positioned within the housing substantially parallel to the central axis and defining an extrafilamentary space within the housing, each of the hollow filaments formed of a material which allows molecular transport therethrough, the housing further comprising a filament inlet port and a filament outlet port, said ports communicating through the hollow filaments to define a filament flow path, and a housing inlet port and a housing outlet port, said ports communicating through the extrafilamentary space to define an extrafilament flow path, the extrafilament flow path being isolated from the filament flow path such that a material in one path may enter the other path only by molecular transport through the material comprising the hollow filaments;

b) providing a cell population positioned within the housing, the cell population occupying the extrafilamentary space and comprising living cells; and c) introducing a volume of a gellable material into the housing in a manner such that, upon gelling, the resulting gel will form a plug positioned in the extrafilament flow path to maintain a substantially uniform flow across the extrafilament flow path, the plug being configured to prevent the cells from exiting the housing through the housing outlet port.

* * * * *